(12) United States Patent
Yamanouchi et al.

(10) Patent No.: US 11,317,922 B2
(45) Date of Patent: May 3, 2022

(54) FILLER MATERIAL, FILLER DELIVERY DEVICE, AND FILLER DELIVERY METHOD

(71) Applicants: KAWASUMI LABORATORIES, INC., Saiki (JP); Dai Yamanouchi, Verona, WI (US)

(72) Inventors: Dai Yamanouchi, Verona, WI (US); Takashi Yoshimori, Bungo-ono (JP)

(73) Assignees: KAWASUMI LABORATORIES. INC., Saiki (JP); Dai Yamanouchi, Verona, WI (US)

( * ) Notice: Subject to any disclaimer, the term of this patent is extended or adjusted under 35 U.S.C. 154(b) by 129 days.

(21) Appl. No.: 16/352,259

(22) Filed: Mar. 13, 2019

(65) Prior Publication Data

US 2019/0298390 A1     Oct. 3, 2019

Related U.S. Application Data

(60) Provisional application No. 62/649,755, filed on Mar. 29, 2018.

(51) Int. Cl.
    *A61B 17/12*          (2006.01)

(52) U.S. Cl.
    CPC .. *A61B 17/12195* (2013.01); *A61B 17/12118* (2013.01); *A61B 17/12186* (2013.01); *A61B 2017/1205* (2013.01)

(58) Field of Classification Search
    CPC ........ A61B 17/12118; A61B 17/12195; A61B 17/12186; A61B 17/12181; A61B 17/12177; A61B 17/12168; A61B 17/12159; A61B 17/12163; A61B 17/1214; A61B 17/12109; A61B 17/12031; A61B 17/12036; A61B 17/1204; A61B 2017/1205; A61B 2017/12086; A61B 2017/12054; A61B 2017/12077; A61B 2017/12068; A61B 2017/12095; A61B 2017/1209

See application file for complete search history.

(56) References Cited

U.S. PATENT DOCUMENTS

2015/0359549 A1*   12/2015   Lenker ............. A61B 17/12118
                                                                 600/585

FOREIGN PATENT DOCUMENTS

JP            2013-106829 A      6/2013

\* cited by examiner

*Primary Examiner* — Erich G Herbermann
(74) *Attorney, Agent, or Firm* — Sughrue Mion, PLLC (57) ABSTRACT

A filler delivery device is configured to place a filler inside a bulge occurring in a body lumen. The filler delivery device includes a frame member configured to be expandable and compressible, and a tubular member through which a catheter for injecting the filler into the bulge is insertable. The tubular member is provided such that, when the frame member is in an expanded state, an open end of the tubular member is directed in a direction intersecting an extending direction of the body lumen. The filler material includes a base gel having flowability with which the filler material flows inside the catheter, and shape retainability with which the filler material stays inside the bulge after being injected from the catheter into the bulge, and a solidification promoting substance that promotes solidification of blood inside the bulge.

3 Claims, 5 Drawing Sheets

FILLER MATERIAL, FILLER DELIVERY DEVICE, AND FILLER DELIVERY METHOD

CROSS-REFERENCE TO RELATED APPLICATION

This application claims benefit to U.S. Provisional Application No. 62/649,755 filed on Mar. 29, 2018, the entire content of which is incorporated herein by reference.

FIELD OF INVENTION

The present invention relates to a filler material to be injected into a bulge occurring in a body lumen using a catheter, a filler delivery device configured to place the filler material inside the bulge, and a filler delivery method for placing the filler inside the bulge by using the filler delivery device.

RELATED ART

A conventionally known treatment method suppresses an enlargement of a bulge occurring in a wall of a blood vessel by blocking blood from flowing into the bulge. Examples of a treatment device for this kind of treatment method include fine metal wires to be placed to fill an internal space of the bulge and to occlude the bulge (see, e.g., JP2013-106829A). Such fine metal wires are sometimes called metal coils.

When using metal coils as a device for treating a bulge, depending on a size of the bulge, it may be necessary to repetitively place a plurality of metal coils, each having a predetermined length, into the bulge. This kind of treatment however is not preferred from a viewpoint of both a burden on a patient's body and medical economy. In addition, when imaging such as CT and MRI is performed after the placement of indwelling metal coils, imaging noise (so-called artifact) may be generated around the metal coils.

Other examples of treatment means for occluding the bulge include gelatin sponge, cyanoacrylate and a dimethyl sulfoxide solution of ethylene-vinyl alcohol copolymer (a DMSO solution of EVOH). However, when using the gelatin sponge, the treatment sometimes becomes complex like in the case of metal coils. When using the cyanoacrylate, the treatment may become difficult due to strong adhesion of the cyanoacrylate. When using the DMSO solution of EVOH, a filler delivery device may be deteriorated if a catheter other than a DMSO-compatible catheter is used, and besides, the allowable amount to be used is limited due to a safety issue of the DMSO.

As such, the conventional treatment means for occluding a bulge has room for improvement in terms of, for example, ease of handling, etc.

SUMMARY

Illustrative aspects of the present invention provide a filler material, a filler delivery device and a filler delivery method, according to which a treatment for suppressing an enlargement of a bulge occurring in a body lumen can be made easier than before.

According to an illustrative aspect of the present invention a filler material is to be injected, using a catheter, into a bulge occurring in a body lumen. The filler material includes a base gel having flowability with which the filler material flows inside the catheter, and shape retainability with which the filler material stays inside the bulge after being injected from the catheter into the bulge, and a solidification promoting substance that promotes solidification of blood inside the bulge.

According to another illustrative aspect of the present invention a filler delivery device is configured to place a filler inside a bulge occurring in a body lumen. The filler delivery device includes a frame member configured to be expandable and compressible, and a tubular member through which a catheter for injecting the filler into the bulge is insertable. The tubular member is provided such that, when the frame member is in an expanded state, an open end of the tubular member is directed in a direction intersecting an extending direction of the body lumen.

According to another illustrative aspect of the present invention a filler delivery method is for injecting a filler into a bulge occurring in a body lumen to place the filler inside the bulge. The filler delivery method includes expanding the frame member of the filler delivery device to cause the frame member to contact and press the inner surface of the body lumen or the inner surface of the tubular indwelling device placed in the body lumen, moving the catheter toward the open end, the catheter being inserted through the tubular member of the filler delivery device, and injecting the filler into the bulge from a distal end portion of the catheter that has passed through the open end of the tubular member.

DETAILED DESCRIPTION

Figure 1:
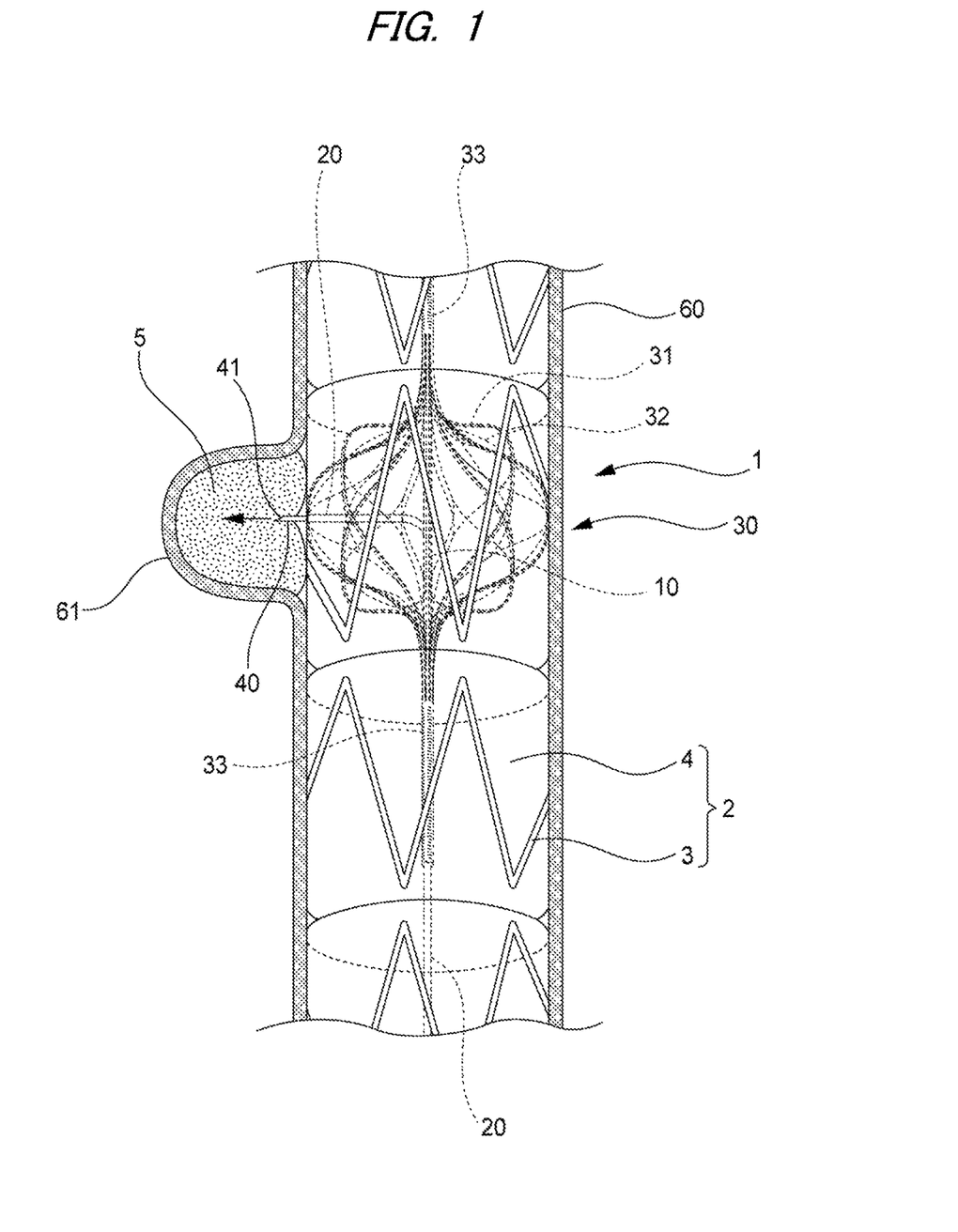
FIG. 1 is a schematic view illustrating how a filler material according to an embodiment of the present invention is injected into a bulge occurred in a blood vessel through a catheter using a filler delivery device according to an embodiment of the present invention in a state in which a stent graft is disposed to cover the bulge.

FIG. 1 illustrates how a filler 5 is injected into a bulge 61 in a blood vessel 60 (such as an aortic aneurysm) of a human body to be placed inside the bulge 61 through a catheter 40 by using a filler delivery device 1 in a state in which a stent graft 2 is placed at a site where the bulge 61 has occurred. By occluding an internal space of the bulge 61 by the filler 5, blood is blocked from flowing into the bulge 61 so that an enlargement of the bulge 61 can be suppressed.

In the following description, when referring to FIGS. 1 to 4, the lower side of the drawing sheets will be referred to as a proximal side and the upper side of the drawing sheets will be referred to as a distal side for convenience of explanation.

Filler

First, the filler 5 will be described.

The filler (filler material) 5 includes a base gel having flowability and shape retainability, a solidification promoting substance that promotes solidification of blood, and a visualization substance having low X-ray transmittance.

The base gel is made of a polymer for example, and forms a base of the filler 5 exhibiting sol-gel transition. Specifically, the base gel has the flowability with which the filler 5 can flow inside the catheter 40, and the shape retainability with which the filler 5 can stay in the bulge 61 after being injected into the bulge 61 from the catheter 40.

The "flowability" and the "shape retainability" can be controlled, for example, by changing the physical property and the chemical property in accordance with components and a manufacturing method of the base gel.

That is, in order to control the flowability with which the filler 5 can flow inside the catheter 40 or to control the shape retainability with which the filler 5 can stay in the bulge 61, it is preferable that the base gel be configured to have at least one of pseudoplasticity, shear thinning and thixotropy. The base gel has such a property that liquid viscosity of the base gel decreases (is softened) in a pressed state in which external force is applied to the base gel, e.g. the base gel is pressed by a syringe, or the viscosity of the base gel changes over time. With this property, the filler 5 can be suitably injected into the bulge 61 and the blood in the bulge 61 can be suitably solidified due to the solidification promoting substance.

Further, in order to control the flowability with which the filler 5 can flow inside the catheter 40 or to control the shape retainability with which the filler 5 can stay in the bulge 61, it is preferable that the base gel is configured to have temperature responsiveness with which the base gel can be cured by a temperature increase. For example, the filler 5 which has not been injected into the bulge 61 yet is in a liquid state under a comparatively low temperature environment like a storage place (such as the inside of an operating room) of the filler 5. After being injected into the bulge 61, the filler 5 is gelled by increasing the temperature to body temperature (e.g., to about 36° C. to 37° C.). With this property, the filler 5 can be suitably injected into the bulge 61 and the blood in the bulge 61 can be suitably solidified due to the solidification promoting substance.

Further, in order to control the flowability with which the filler 5 can flow inside the catheter 40 or to control the shape retainability with which the filler 5 can stay in the bulge 61, it is preferable that the base gel be configured to be cured by contact with water. For example, the base gel may be configured to contain a softening agent eluted by contact with a water content of the blood. In this case, the filler 5 is in a liquid state when the filler 5 flows inside the catheter 40 in order to be injected into the bulge 61. After the filler 5 is injected into the bulge 61, the softening agent of the base gel is eluted by contact with the blood and the base gel is therefore gelled.

It is preferable that a time until the filler 5 injected into the bulge 61 is gelled be set to be varied also in accordance with a kind of a tubular indwelling device (e.g., a stent graft, a stent, etc.) to be placed in the blood vessel (body lumen) 60. For example, when the stent graft is used for treatment of the bulge 61 (hematocele) in the blood vessel 60, it is considered that the time until the filler 5 is gelled may be long because the bulge 61 is in a closed state in which the bulge 61 is partitioned by an outer wall of the stent graft. When the stent is used for treatment of the bulge 61 in the blood vessel 60, it is considered that the time until the filler 5 is gelled is preferably set to be shorter because the bulge 61 is disposed in an open state.

The solidification promoting substance promotes solidification of the blood present inside the bulge 61.

Here, the "solidification" is a concept that contains, for example, an increase of viscosity, coagulation, hardening, organization, thrombus formation, fibrosis formation, embolus formation, etc. of the blood.

Specifically, it is preferable that the solidification promoting substance include at least one of calcium and a substance having a negatively charged surface. Instead of the calcium or in addition to the calcium, the solidification promoting substance may further include a blood coagulation promoting substance such as gelatin, collagen and silica. An action mechanism of the substance having the negatively charged surface includes a factor XII, a serine protease precursor, being transformed into an active protease by contacting the negatively charged surface so that intrinsic blood coagulation cascade reaction is started.

Further, it is preferable that the solidification promoting substance include at least one of a blood coagulation factor and a fibroblast growth factor. Due to the filler material 5 containing the solidification promoting substance, for example, heparinization of a patient can be neutralized so that solidification (thrombus formation or organization) of the blood in the bulge 61 can be made to proceed rapidly. Particularly, due to the fibroblast growth factor contained in the filler material, fibrosis of the blood where thrombus has been formed can be promoted and organization in the bulge 61 can be promoted.

Examples of the visualization substance include barium sulfate powder, tungsten powder, gold powder, platinum powder, iridium powder, bismuth power and the like, but they are merely non-limiting examples, and may optionally be changed as appropriate. By adjustment of a material and a content of the visualization substance, imaging noise generated during imaging based on CT etc. can be suppressed more greatly than that in the case where the metal coils are used.

Stent Graft

Next, a configuration of the stent graft 2, and a configuration of the filler delivery device 1 for placing the filler material 5 will be described sequentially.

As shown in FIG. 1, the stent graft 2 has a tubular shape defining a passage through which a blood flow can pass. The stent graft 2 includes a frame portion 3 and a membrane 4. The stent graft 2 may have a linear tubular shape or a curved tubular shape (e.g., in a shape corresponding to a shape of a blood vessel of a patient) as necessary. The stent graft 2 may be prepared to have a curved shape in accordance with a predetermined placement site before being placed or may have a shape that is curved to follow the shape of the blood vessel after being placed.

The frame portion 3 is configured into a self-expandable type wire mesh shape in which thin metal wires are folded zigzag and molded into a tubular shape. With such a configuration, the frame portion 3 can be deformed from a compressed state in which the frame portion 3 is compressed radially inward, into an expanded state in which the frame portion 3 is expanded radially outward so that a tubular passage can be defined. Examples of the material of the frame portion 3 includes known metals or metal alloys, such as stainless steel, an Ni—Ti alloy, and a titanium alloy.

The membrane 4 is fixed to the frame portion 3 so as to cover the frame portion 3 along the frame portion 3, and defines the tubular passage. Examples of the material of the membrane 4 include a fluororesin such as polytetrafluoroethylene (PTFE), a polyester resin such as polyethylene terephthalate, and the like.

As will be described later, the stent graft 2 is placed at a site where the bulge 61 in the blood vessel 60 shown in FIG. 1 has occurred, using a stent delivery device 70 for placing the stent graft 2 at a predetermined position in the blood vessel.

Filler Delivery Device

As shown in FIG. 1 and FIGS. 2A to 2D, the filler delivery device 1 includes a tubular sheath 10, a tubular member 20 and a frame member 30. The tubular member 20 is inserted through a hollow space of the sheath 10. The frame member 30 is disposed on an outer circumference of an axial (longitudinal) portion of the sheath 10.

The sheath 10 is formed out of a flexible material. Examples of the flexible material include biocompatible synthetic resins (elastomers) that are selected from a fluororesin, a polyamide-based resin, a polyethylene-based resin, a polyvinyl chloride-based resin, etc., resin compounds in which other materials are mixed with these resins, multilayer structure bodies of these synthetic resins, complexes of these synthetic resins and metal wires, and the like. A lumen (narrow hole) for inserting a guide wire 50 (see FIGS. 3D and 3E) therethrough is formed at a portion of a thick portion of the sheath 10 to axially penetrate the sheath 10.

A catheter 40 can be inserted through a hollow space of the tubular member 20 so as to be movable back and forth. An outer diameter of the tubular member 20 is smaller than an inner diameter of the sheath 10. Therefore, the tubular member 20 can be moved in the axial direction of the sheath 10 relatively to the sheath 10. The tubular member 20 is also formed out of a flexible material in a similar manner to or the same manner as the sheath 10. The same material as the material of the sheath 10 can be used as the material of the tubular member 20. A distal side open end 21 of the tubular member 20 is extended to the outside of the sheath 10 through a side surface opening 11 provided in a side surface of the sheath 10, as shown in FIG. 2C, so that the distal side open end 21 of the tubular member 20 is joined to one of undermentioned main wire elements 31 of the frame member 30, as shown in FIG. 2D. A structure in the vicinity of the end portion 21 of the tubular member 20 will be described later in more detail.

Figure 2A:
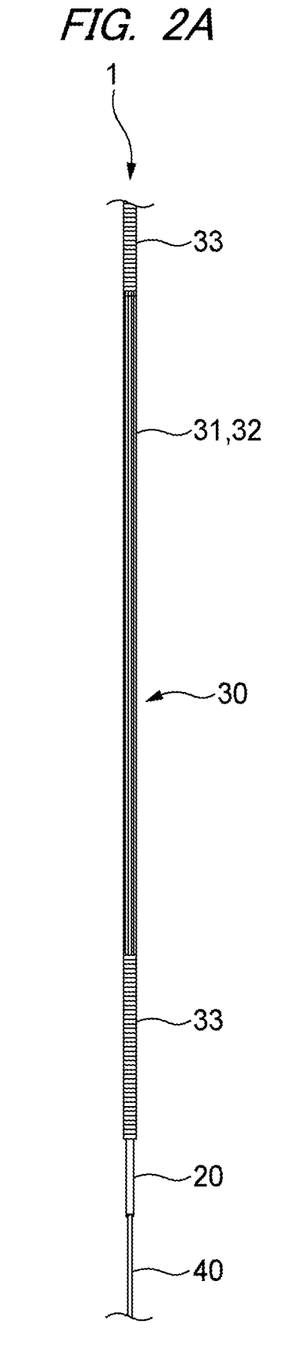
FIG. 2A is a side view of the filler delivery device with a frame member being in a compressed state.
Figure 2B:
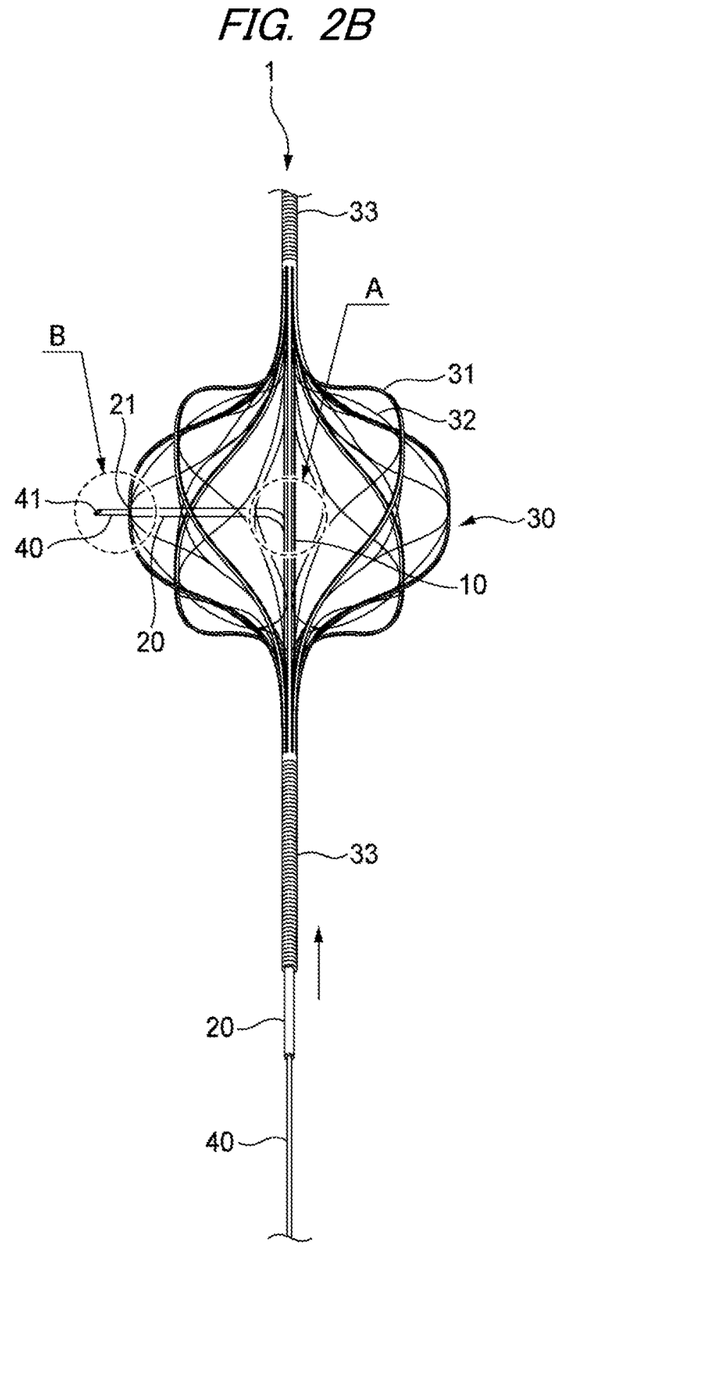
FIG. 2B is a side view of the filler delivery device with the frame member being in an expanded state.
Figure 2C:
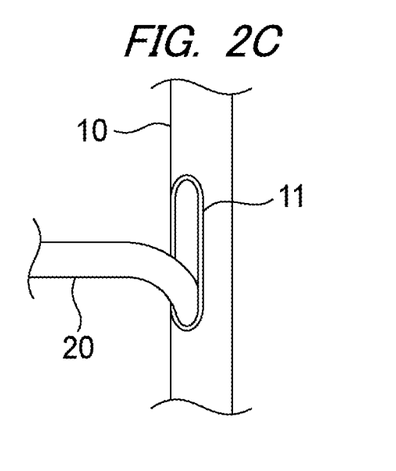
FIG. 2C is an enlarged view of a portion A in FIG. 2B.
Figure 2D:
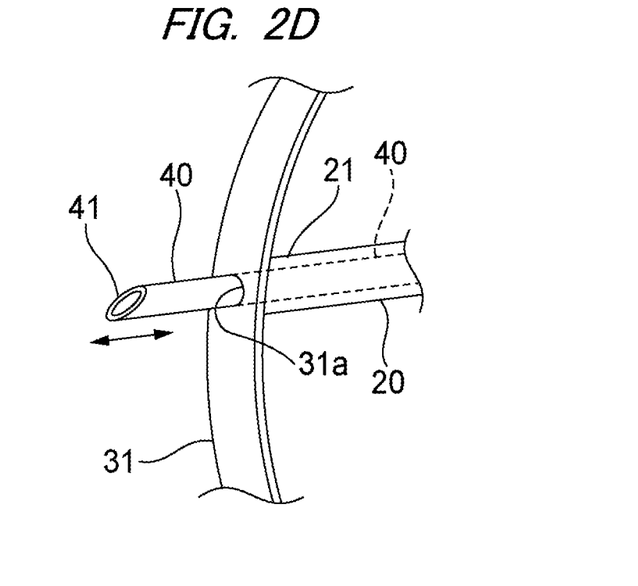
FIG. 2D is an enlarged view of a portion B in FIG. 2B.

The frame member 30 is configured to be compressible to a compressed state in which the frame member 30 is compressed radially inward as shown in FIG. 2A, and expandable to an expanded state in which the frame member 30 is expanded radially outward as shown in FIG. 2B. Thus, the frame member 30 can be shifted from the compressed state to the expanded state at a place where the stent graft 2 has been already placed in the blood vessel 60, as shown in FIG. 1. As a result, the frame member 30 contacts and presses an inner surface of the stent graft 2 so as to keep the position of the frame member 30 inside the blood vessel 60.

The frame member 30 has a plurality of main wire elements 31 arranged at equal intervals along a circumferential direction of an outer circumference of the sheath 10, a plurality of auxiliary wire elements 32 each connecting the main wire elements 31 that are adjacent to each other in the circumferential direction of the sheath 10, and a pair of cylindrical pipe members 33 provided on the outer circumference of the sheath 10 and joined to longitudinal end portions of each of the main wire elements 31.

A sectional shape of each of the main wire elements 31 and the auxiliary wire elements 32 is, for example, substantially rectangular. A sectional area of the main wire element 31 is larger than a sectional area of the auxiliary wire element 32. Therefore, rigidity of the main wire element 31 is higher than rigidity of the auxiliary wire element 32. Examples of the material of the main wire element 31 and the auxiliary wire element 32 include known metals or metal alloys such as stainless steel, an Ni—Ti alloy, and a titanium alloy. In addition, the main wire element 31 and the auxiliary wire element 32 are made of a material having super elasticity (a property with which even when the main wire element 31 or the auxiliary wire element 32 is deformed, it can be restored to its original shape as soon as force is removed). The Ni—Ti alloy is one example of the material having super elasticity.

The pair of pipe members 33 are provided so as to interpose the side surface opening 11 (see FIG. 2C) of the sheath 10 therebetween in the axial direction of the sheath 10. One or each of the pair of pipe members 33 can be moved in the axial direction of the sheath 10 relatively to the sheath 10. Therefore, an interval between the pair of pipe members 33 can be adjusted between a first interval (see FIG. 2A) and a second interval (see FIG. 2B) smaller than the first interval. The interval between the pair of pipe members 33 can be adjusted by use of a not-shown predetermined operating tool. Any operating tool having a known configuration can be used as the operating tool. Accordingly, detailed description about the configuration of the operating tool will be omitted.

When the interval between the pair of pipe members 33 is adjusted to the first interval (see FIG. 2A), the main wire elements 31 and the auxiliary wire elements 32 are disposed to extend linearly in the axial direction of the sheath 10. This state corresponds to the compressed state of the frame member 30. On the other hand, when the interval between the pair of pipe members 33 is adjusted to the second interval (see FIG. 2B), the main wire elements 31 and the auxiliary wire elements 32 are curved so that longitudinally central portions of the main wire elements 31 and the auxiliary wire elements 32 protrude radially outward from the sheath 10. This state corresponds to the expanded state of the frame member 30.

The following configuration may be used as an example of a specific mechanism for expanding and compressing the frame member 30 in the manner described above. That is, the sheath 10 includes a tubular large diameter portion and a tubular small diameter portion that is inserted into the large diameter portion to extend from the large diameter portion toward a distal side so as to be movable axially relatively to the large diameter portion. One of the pipe members 33 on the distal side is joined to an outer circumferential surface of the small diameter portion, and the other of the pipe members 33 on a proximal side is joined to an inner circumferential surface of a distal end portion of the large diameter portion. In this case, when the operating tool is used to adjust an axially relative position of the small diameter portion to the large diameter portion, the interval between the pair of pipe members 33 is adjusted, so that the frame member 30 is expanded or compressed.

For example, any of known metals or metal alloys represented by stainless steel, a titanium alloy, an Ni—Ti alloy, an Ni—Ti—Co alloy, an Ni—Ti—Cu alloy, an Au—Cd alloy, a Cu—Al—Ni alloy, etc. can be preferably used as a material forming the pipe members 33. By using a radiographically visible alloy, the pipe members 33 may function as radiopaque markers. In this case, the positions of the pipe members 33 (i.e., the position of the frame member 30) can be confirmed from the outside of the body. Numberless slits each extending in a direction perpendicular to a tube axis are provided in outer surfaces of the pipe members 33. Thus, flexibility of the pipe members 33 can be improved. A method for forming notches in the outer surfaces of the pipe members 33 may be, for example, laser machining.

A pipe-like material can be formed into the pipe members 33, the main wire elements 31 and the auxiliary wire elements 32 by laser machining. Thus, the pipe members 33, the main wire elements 31 and the auxiliary wire elements 32 can be formed integrally.

As shown in FIGS. 2B to 2D, the distal end portion 21 of the tubular member 20 extended outward from the sheath 10 through the side surface opening 11 of the sheath 10 is joined to the joint place of one main wire element 31 of the main wire elements 31 of the frame member 30. An opening 31*a* communicating with the hollow space of the tubular member 20 is formed in the joint place of the one main wire element 31. Therefore, a distal end 41 of the catheter 40 inserted through the tubular member 20 can enter and leave the opening 31*a* of the main wire element 31, as shown in arrows of FIG. 2D.

As seen from comparison between FIG. 2A and FIG. 2B, when the frame member 30 is in the compressed state, the end portion 21 of the tubular member 20 is positioned in the vicinity of the side surface opening 11 of the sheath 10. When the frame member 30 is shifted from the compressed state to the expanded state, the end portion 21 of the tubular member 20 is pulled out of the side surface opening 11 of the sheath 10 to move radially outward from the sheath 10 as the joint place of the main wire element 31 moves radially outward from the sheath 10. As a result, an opening of the end portion 21 (i.e., the opening 31*a* of the main wire element 31) is disposed to face the radial outside of the sheath 10. In other words, the tubular member 20 is provided such that, when the frame member 30 is in the expanded state, an open end 21 is directed in in a direction intersecting an extending direction of the blood vessel 60.

Therefore, the catheter 40 that has been inserted through the tubular member 20 is advanced toward the open end 21 in the expanded state of the frame member 30. Thus, a distal end 41 of the catheter 40 facing the radial outside of the sheath 10 can be protruded from the opening 31*a* of the main wire element 31, as shown in FIG. 2B and FIG. 2D.

As shown in FIG. 2D, the distal end 41 of the catheter 40 is cut so that a distal end surface of the distal end 41 can be inclined to an axial direction of the catheter 40. Therefore, the distal end 41 of the catheter 40 can be used to break through the membrane 4 of the stent graft 2 already placed in the blood vessel 60 (see FIG. 1 and FIG. 3E).

Steps for Placing Stent Graft and Filler

Next, steps for placing the stent graft 2 and the filler 5 at a site where the bulge 61 has occurred in the blood vessel 60 will be described with reference to FIGS. 3A to 3F.

Figure 3A:
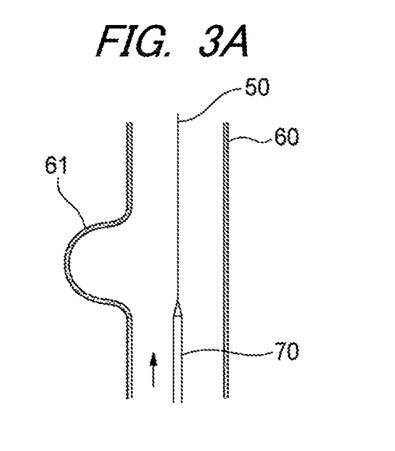
FIGS. 3A to 3F are a series of views illustrating steps for placing the stent graft and the filler material.

First, as preparation, a guide wire 50 that has been disposed to pass through the blood vessel 60 where the bulge 61 has occurred as a diseased part is inserted through a guide wire lumen of the stent delivery device 70 of the stent graft 2. As shown in FIG. 3A, the stent delivery device 70 is advanced toward the site where the bulge 61 has occurred. At this time point, the stent graft 2 is maintained at the compressed state. As the stent delivery device 70 to be used can have a known configuration, detailed description of the configuration of the stent delivery device 70 will be omitted.

Figure 3B:
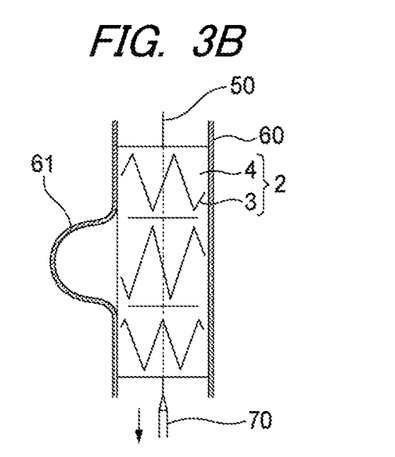

Next, as shown in FIG. 3B, the stent delivery device 70 is operated to bring the stent graft 2 into tight contact with an inner wall surface of the blood vessel 60 including the site where the bulge 61 has occurred while self-expanding the stent graft 2 radially outward. Thus, the stent graft 2 is fixed to the inner wall surface. After the stent graft 2 is expanded and fixed, the stent delivery device 70 is removed while the guide wire 50 is left as it is. Thus, the placement of the stent graft 2 is completed so as to cover a location at which an internal space of the bulge 61 and an internal space of the blood vessel 60 are connected to each other (i.e. an opening portion of the bulge 61). As a result, blood can be blocked at least temporarily from flowing into the bulge 61.

Next, the guide wire 50 is inserted through a guide wire lumen of the sheath 10 in the filler delivery device 1 in which the frame member 30 is in the compressed state. In this state, the catheter 40 is not inserted through the tubular member 20 of the filler delivery device 1. The guide wire 50 is used to advance the filler delivery device 1 as a whole to the site where the bulge 61 in the blood vessel 60 has occurred, as shown in FIG. 3C.

Figures 3C, 3D:
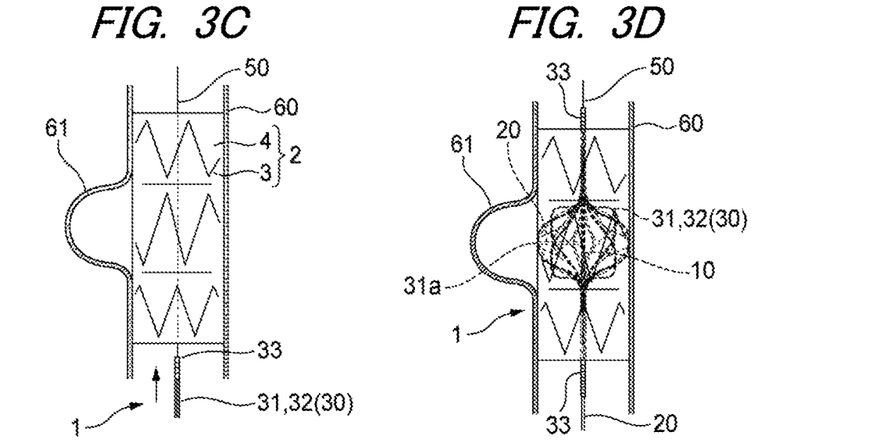

Next, the operating tool (not shown) for compressing and expanding the frame member 30 is operated so as to shift the frame member 30 from the compressed state to the expanded state, as shown in FIG. 3D. Thus, the frame member 30 contacts and presses the inner surface of the stent graft 2 so that the frame member 30 in the expanded state can be retained at the site where the bulge 61 in the blood vessel 60 has occurred. As a result, the opening of the end portion 21 of the tubular member 20 (i.e. the opening 31*a* of the main wire element 31) is disposed to face the internal space of the bulge 61 located radially outside the sheath 10. Thus, according to the filler delivery device 1, the frame member 30 can be disposed accurately at the site where the bulge 61 has occurred.

Figure 3E:
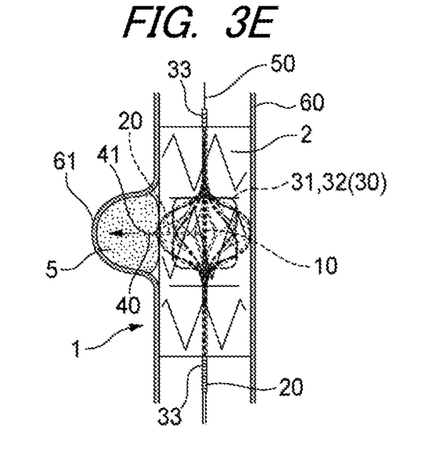

Next, the catheter 40 is inserted through the tubular member 20 from a proximal side of the tubular member 20. The catheter 40 is advanced toward the end portion 21 of the tubular member 20. The distal end 41 of the catheter 40 that has faced the radial outside of the sheath 10 is made to protrude from the opening 31*a* of the main wire element 31, as shown in FIG. 3E.

As a result, the distal end 41 of the catheter 40 breaks through the membrane 4 of the stent graft 2 that has been placed in the blood vessel 60 so that the distal end 41 of the catheter 40 is exposed to the internal space of the bulge 61. In this state, the filler 5 is supplied into the catheter 40 from a proximal side of the catheter 40. The filler 5 flows inside the catheter 40 toward the distal end 41 side in a pressed state so as to be injected into the internal space of the bulge 61 from the distal end 41. The filler 5 is injected into the internal space with an amount sufficient for filling and occluding the internal space of the bulge 61.

Figure 3F:
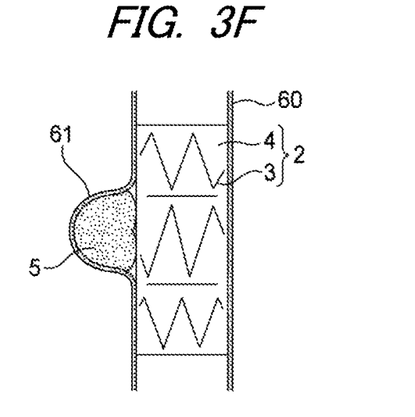

Next, the frame member 30 is returned from the expanded state to the compressed state, and the indwelling device 1 as a whole is removed together with the guide wire 50. Thus, the indwelling of the filler 5 is completed, as shown in FIG. 3F. When the internal space of the bulge 61 is occluded by the filler 5 thus, blood can be more surely blocked from flowing into the bulge 61 so that enlargement of the bulge 61 can be suppressed more greatly. Further, the stent graft 2 is placed to cover the location at which the internal space of the bulge 61 and the internal space of the blood vessel 60 are connected to each other. Accordingly, the filler 5 that has been placed in the internal space of the bulge 61 can be suppressed to the outmost from flowing out to the internal space of the blood vessel 60.

As described above, the filler 5 has the flowability with which the filler 5 can flow inside the catheter 40, and the shape retainability with which the filler 5 can stay in the bulge 61 after being injected into the bulge 61 from the catheter 40. The filler 5 promotes solidification of blood inside the bulge 61. Accordingly, when the filler 5 is injected into the bulge 61, the blood in the bulge 61 is solidified so that the internal space of the bulge 61 can be occluded by the solidified blood. Thus, a necessary amount of the filler 5 may just have to be injected regardless of the size of the bulge 61, in comparison with that in the case where, for example, the metal coils are used to occlude the internal space of the bulge 61 as in the background art. Accordingly, a treatment is made easier. In addition, imaging noise during imaging using CT etc. is hardly generated. In addition, as compared with the cyanoacrylate and the DMSO solution the, the base gel and the solidification promoting substance are less likely to affect the filler delivery device 1. Accordingly, a treatment for suppressing enlargement of the bulge 61 that has occurred in the blood vessel 60 can be made easier than before.

Further, the bulge 61 is occluded by the filler 5. Thus, blood can be more surely suppressed from flowing into the bulge 61 (so-called endoleak) through a gap between the stent graft 2 and the inner surface of the blood vessel 60 and a postoperative long-term result can be further improved, in comparison with a case where the bulge 61 is occluded by only the stent graft 2. In addition, the bulge 61 can be treated even when treatment using only the stent graft is anatomically difficult, for example, due to a short sealing zone. In addition, the internal space of the bulge 61 can be substantially eliminated due to formation of thrombus or fibrosis inside the bulge 61. Accordingly, frequency of postoperative CT imaging inspection for checking presence/absence of the end leak can be reduced.

The present invention is not limited to the foregoing embodiment, and but various modifications may be implemented within the scope of the present invention. For example, the present invention is not limited to the foregoing embodiment, and changes and modifications may be made therein as appropriate. Moreover, the materials, shapes, dimensions, numbers, arrangement locations, and the like of the respective elements of the foregoing embodiment are optional and non-limiting as long as they can achieve the present invention.

For example, in the foregoing embodiment, the filler 5 is placed in the bulge 61 with the catheter 40 using the filler delivery device 1 in the state in which the stent graft 2 is already placed at a site where the bulge 61 has occurred in the blood vessel 60. However, the stent graft 2 need not be placed in advance. That is, the filler 5 may be directly placed in the bulge 61 using the filler delivery device 1 without using the stent graft 2. In this case, by shifting the frame member 30 from the compressed state to the expanded state, the frame member 30 directly contacts the inner surface of the blood vessel 60, so as to keep the position of the frame member 30 inside the blood vessel 60.

Figure 4:
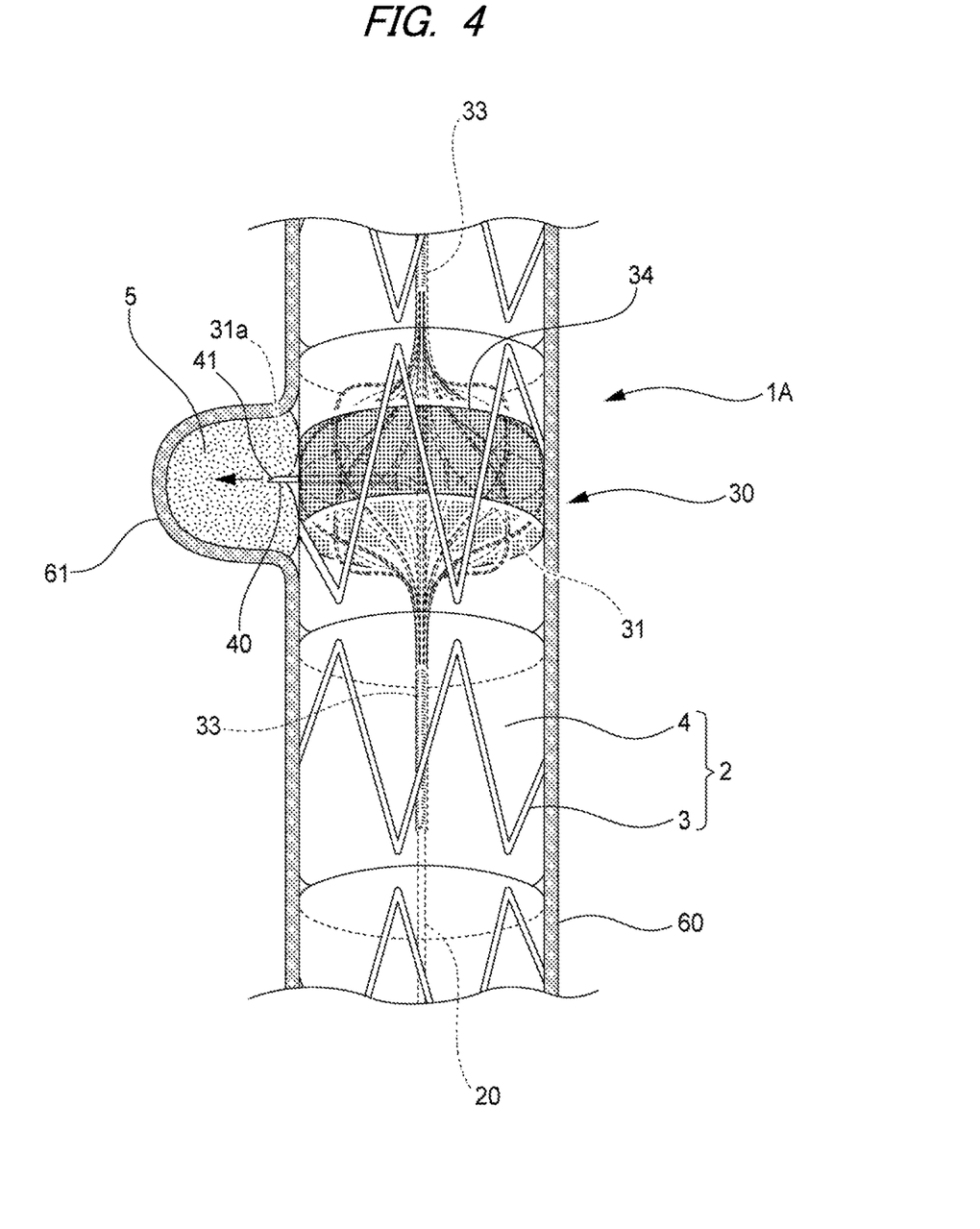
FIG. 4 is a schematic view illustrating a modification of the filler delivery device.

In addition, in the foregoing embodiment, the frame member 30 may press the stent graft 2 that has been placed in the blood vessel 60, radially outward from the inside to expand the stent graft 2. That is, as shown in FIG. 4, an filler delivery device 1A may have a function of not only making a frame member 30 to contact and pressure an inner surface of a stent graft 2 to keep the position of the frame member 30 in a blood vessel 60 when injecting the filler 5 into the bulge 61, but also, for example, further expanding the stent graft 2 that has been insufficiently expanded inside the blood vessel 60 by increasing expansion force of the frame member 30.

Here, when a frame member 3 is not covered with a membrane 4 but exposed in the inner surface of the stent graft 2, the frame portion 3 may be damaged or tangled by contacting the main wire elements 31 of the frame member 30. To solve this problem, for example, a ring-shaped sheet 34 may be provided on an outer side of a portion forming a largest outer diameter of the main wire elements 31 of the frame member 30. The sheet 34 is, for example, an elastically deformable member made of a biocompatible material such as a fluororesin such as PTFE, a polyester resin such as PET, nylon, a silicon resin, etc. In addition, the shape of the sheet 34 does not always have to be annular, and may be a shape that can be provided only on portions of the main wire elements 31 at least making contact with the frame portion 3.

Thus, the stent graft 2 can be expanded properly using the filler delivery device 1A regardless of the structure of the stent graft 2.

For example, an opening (not shown) through which the catheter 40 can be inserted may be formed in a portion of the sheet 34 corresponding to an opening portion 31a of one of the main wire elements 31, or the portion of the sheet 34 may be broken through by use of a distal end 41 of the catheter 40 when a filler 5 is injected into the bulge 61.

Further, in the foregoing embodiment, the filler delivery device 1 and the filler 5 are used for the blood vessel 60. Other than the aorta exemplified in the foregoing embodiment, the blood vessel 60 may be a cerebral artery. In addition, the filler delivery device 1 and the filler 5 may be used for any other body lumen than the blood vessel, such as an alimentary canal, a ureter, or the like of the living body.

Further, while the filler 5 containing the visualization substance having low X-ray transmittance has been described as an example in the foregoing embodiment, this is merely a non-limiting example, and whether the filler contains the visualization substance or not can be selected optionally as appropriate.

Further, while the frame member 30 of the filler delivery device 1 has been described as having the main wire elements 31 and the auxiliary wire elements 32 in the foregoing embodiment, this is merely a non-limiting example, and the configuration of the frame member 30 can be changed optionally as appropriate. That is, the frame member 30 can have any configuration as long as it is configured to be expandable and compressible, and does not always have to have the main wire elements 31 and the auxiliary wire elements 32.

Further, the case where the tubular member 20 is inserted through the hollow space of the sheath 10 and the distal end portion 21 of the tubular member 20 is joined to one of the main wire elements 31 of the frame member 30 has been illustrated. This is merely an example, and the present invention is not limited thereto. The configuration of the tubular member 20 can be changed suitably and desirably. That is, the tubular member 20 may have any configuration as long as the tubular member 20 can be provided such that, when the frame member 30 is in the expanded state, an open end of the tubular member 20 is directed in the direction intersecting the extending direction of the body lumen (blood vessel). The tubular member 20 does not always have to be inserted through the hollow space of the sheath 10 or the distal end portion 21 of the tubular member 20 does not always have to be joined to the main wire element 31 of the frame member 30.

What is claimed is:
1. A filler delivery device configured to place a filler inside a bulge occurring in a body lumen, the filler delivery device comprising:
   a frame member configured to be expandable and compressible; and
   a tubular member through which a catheter for injecting the filler into the bulge is insertable,
   wherein the frame member includes a plurality of main wire elements and a plurality of auxiliary wire elements connecting the main wire elements to each other, wherein a distal end of the tubular member is joined to an inside surface of the frame member, and the inside surface of the frame member includes a joint place between one of the plurality of the main wire elements and the distal end of the tubular member, wherein the tubular member is provided such that, when the frame member is in an expanded state, an open end of the tubular member is directed in a direction intersecting an extending direction of the body lumen, and a distal end of the catheter is capable of being protruded from and drawn into the open end.

2. The filler delivery device according to claim 1, wherein the frame member is configured to contact and press, when the frame member is in the expanded state, an inner surface of the body lumen or an inner surface of a tubular indwelling device placed inside the body lumen so as to keep a position of the frame member inside the body lumen.

3. A filler delivery method for injecting a filler into a bulge occurring in a body lumen to place the filler inside the bulge using a filler delivery device, the filler delivery device having a frame member configured to be expandable and compressible, and a tubular member through which a catheter for injecting the filler into the bulge is insertable, the frame member including a plurality of main wire elements and a plurality of auxiliary wire elements connecting the main wire elements to each other, a distal end of the tubular member being joined to an inside surface of the frame member, the inside surface of the frame member including a joint place between one of the plurality of the main wire elements and the distal end of the tubular member, and the tubular member being provided such that, when the frame member is in an expanded state, an open end of the tubular member is directed in a direction intersecting an extending direction of the body lumen, the filler delivery method comprising:

expanding the frame member to cause the frame member to contact and press an inner surface of the body lumen or an inner surface of a tubular indwelling device placed in the body lumen;

moving the catheter toward the open end of the tubular member, the catheter being inserted through the tubular member of the filler delivery device; and     injecting the filler into the bulge from a distal end portion of the catheter that has passed through the open end of the tubular member.

\* \* \* \* \*